(12) United States Patent
Krueger et al.

(10) Patent No.: US 12,201,329 B2
(45) Date of Patent: Jan. 21, 2025

(54) METHOD AND DEVICE FOR ENDOSCOPIC ENDONASAL OCCIPITOCERVICAL FUSION

(71) Applicant: University of Cincinnati, Cincinnati, OH (US)

(72) Inventors: Bryan Matthew Krueger, Cincinnati, OH (US); Owen Andrew Yager, Louisville, KY (US); Justin Louis Gibson, Cincinnati, OH (US); Roger Hartl, New York, NY (US)

(73) Assignee: University of Cincinnati, Cincinnati, OH (US)

( * ) Notice: Subject to any disclaimer, the term of this patent is extended or adjusted under 35 U.S.C. 154(b) by 163 days.

(21) Appl. No.: 17/433,659

(22) PCT Filed: Feb. 25, 2020

(86) PCT No.: PCT/US2020/019709
§ 371 (c)(1),
(2) Date: Aug. 25, 2021

(87) PCT Pub. No.: WO2020/176514
PCT Pub. Date: Sep. 3, 2020

(65) Prior Publication Data
US 2022/0039840 A1  Feb. 10, 2022

Related U.S. Application Data

(60) Provisional application No. 62/810,035, filed on Feb. 25, 2019.

(51) Int. Cl.
*A61B 17/70*  (2006.01)

(52) U.S. Cl.
CPC ............... *A61B 17/7055* (2013.01)

(58) Field of Classification Search
CPC .................................. A61B 17/7055
See application file for complete search history.

(56) References Cited

U.S. PATENT DOCUMENTS

| | | | |
|---|---|---|---|
| 2004/0249377 A1* | 12/2004 | Kaes | A61F 2/4455 606/279 |
| 2005/0209599 A1 | 9/2005 | Brunsvold | |
| 2006/0235403 A1* | 10/2006 | Blain | A61B 17/86 606/295 |
| 2008/0215093 A1 | 9/2008 | Lin et al. | |

(Continued)

OTHER PUBLICATIONS

Ihab Zidan, Wael Fouad. Occipitocervical fixation in the management of craniocervical instabilities. Alexandria Journal of Medicine, vol. 47, Issue 3, 2011, pp. 185-192.

(Continued)

*Primary Examiner* — Tessa M Matthews
(74) *Attorney, Agent, or Firm* — Brent M. Peebles

(57) ABSTRACT

A novel endonasal method for occipitocervical fusion is provided. This new method provides a minimally invasive advance in the ability of surgeons to treat pathology of the craniocervical junction. The method uses an implant system comprising a body having a spacer section that engages with the occipital condyle and a plate section that engages with the C1 lateral mass. Fasteners fix the plate section with the occipital condyle the plate section with the C1 lateral mass.

16 Claims, 14 Drawing Sheets

(56) References Cited

U.S. PATENT DOCUMENTS

2008/0300634 A1* 12/2008 Gray .................... A61F 2/4455
606/264
2012/0185047 A1 7/2012 Wooley
2015/0032220 A1* 1/2015 Tyber .................... A61F 2/4455
623/23.5

OTHER PUBLICATIONS

International Search Report mailed Jun. 10, 2020 and Written Opinion in Intl. Patent Application No. PCT/US2020/019709 filed Feb. 25, 2020. 6 pgs.

* cited by examiner

METHOD AND DEVICE FOR ENDOSCOPIC ENDONASAL OCCIPITOCERVICAL FUSION

CROSS REFERENCE TO RELATED APPLICATIONS

This application is a continuation of PCT Application No. PCT/US20/19709 filed Feb. 25, 2020, which claims benefit of U.S. Provisional Application Ser. No. 62/810,035, filed Feb. 25, 2019, which application is hereby incorporated by reference in its entirety.

TECHNICAL FIELD

The present invention relates to a method and device for occipitocervical fusion. More specifically, this invention relates to an endoscopic endonasal surgical approach for occipitocervical fusion.

BACKGROUND OF THE INVENTION

Conditions in which the odontoid ventrally compresses the brainstem or spinal cord such as in trauma, rheumatoid arthritis pannus formation, basilar invagination and Chiari 1 malformation often present as lower cranial neuropathies, sensorimotor deficits and/or myelopathy necessitating decompression and subsequent stabilization and fusion. Following endonasal odontoidectomy, it is common for patients to require arthrodesis across O-C1 and C1-2. Traditionally, arthrodesis across O-C1 and C1-2 has been performed with posterior instrumentation and fusion as a second stage. Recent cadaveric feasibility studies have described endoscopic endonasal methods for C1-2 fixation. To date, however, no validated method for endonasal O-C1 exists.

SUMMARY OF THE INVENTION

The present invention is a novel endonasal method for occipitocervical fusion. One embodiment of the present invention is an implant system that enables atlanto-occipital fixation. This new method provides a minimally invasive advance in the ability of surgeons to treat pathology of the craniocervical junction.

In one embodiment, the implant system of the present invention comprises a body having a spacer section and a plate section. The spacer section has an occipital condyle engaging surface and a C1 lateral mass engaging surface. The occipital condyle engaging surface is disposed relative to the C1 lateral mass engaging surface at a selected angular orientation. The plate section defines at least a first opening and a second opening. The implant system also has at least two bone fixation fasteners; a first fastener disposed with the first opening, and a second fastener disposed with the second opening. The first fastener is engageable with the plate section and capable of fixing with the occipital condyle and the second fastener is engageable with the plate section and capable of fixing with the C1 lateral mass.

In an embodiment, the implant system also includes at least a first washer and a second washer. The first washer is disposed with the first opening and the second washer is disposed with the second opening. In another embodiment, the selected angular orientation of the occipital condyle engaging surface relative to the C1 lateral mass engaging surface is from about 10 degrees to about 20 degrees.

In another embodiment, the first opening and the second opening are threaded bore holes. In one embodiment, the threaded bore holes of the first and second openings direct the first and second fasteners at the same angular orientation. In another embodiment, the threaded bore holes of the first and second openings direct the first and second fasteners at different angular orientations.

In another embodiment, the occipital condyle engaging surface and the C1 lateral mass engaging surface have projections selected from the group consisting of teeth, ridges, spikes and combinations thereof.

In an embodiment, the spacer section has one or more graft holes. In some embodiments, the graft hole is from about 3 to about 5 mm wide and about 8 to about 12 mm long. In an embodiment, the graft hole contains autograft, allograft or a combination thereof.

In another embodiment, implant system comprises two or more bodies having the same configuration. In an embodiment, the body comprises a material selected from the group consisting of carbon fiber, polylactic acid, stainless steel alloys, commercially pure titanium, titanium alloys, ceramics, thermoplastics, polyethylene terephthalate (PET), fabric, silicone, polyurethane, silicone-polyurethane copolymers, polymeric rubbers, polyolefin rubbers, hydrogels, semi-rigid and rigid materials. In one embodiment, the body comprises carbon fiber.

In an embodiment, the bone fixation fasteners are selected from the group consisting of bone screws, helical nails, distally expanding nails, and distally expanding screws.

The present invention also discloses a novel atlanto-occipital fusion method for fixating a 0-C1 joint. In one embodiment, the method comprises a) preparing an endonasal surgical path using a binostril approach comprising i) removing the inferior portion of the posterior septum, ii) performing a myomucosal flap incision to create a flap, and iii) retracting the flap to expose the O-C1 joint. Then, b) bilaterally decorticating the O-C1 joint, c) drilling a nutrient hole in the occipital condyle, and d) inserting an implant into each side of the decorticated 0-C1 joint. The implant comprises the implant system described above.

In another embodiment, the inserted implant is supported by the cortex of the C1 lateral mass joint articulating surface posteriorly and a rim of cortex of the anterior wall of C1 lateral mass anteriorly.

BRIEF DESCRIPTION OF THE DRAWINGS

The foregoing summary, as well as the following detailed description of preferred embodiments of the application, will be better understood when read in conjunction with the appended drawings. For the purposes of illustrating the implant of the present application, there is shown in the drawings preferred embodiments. It should be understood, however, that the application is not limited to the precise arrangements and instrumentalities shown. In the drawings:

FIG. 5 illustrate various perspective views of additional blocking plate geometries and securing mechanisms;

DETAILED DESCRIPTION OF THE INVENTION

Figure 1:
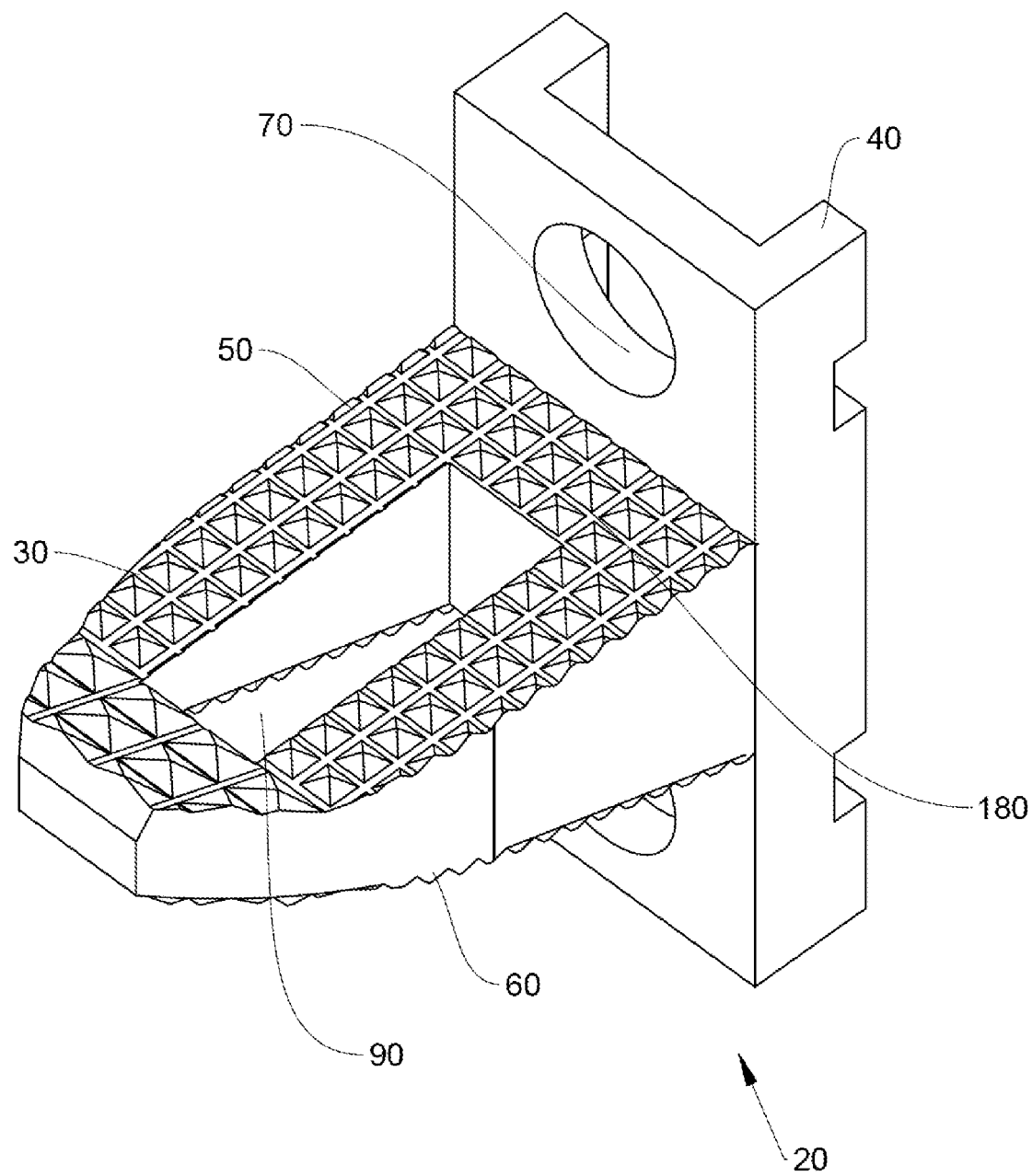
FIG. 1 illustrates a posterior perspective view of an implant according to an embodiment of the present application.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

Certain terminology is used in the following description for convenience only and is not limiting. The words "right", "left", "lower" and "upper" designate directions in the drawings to which reference is made. The words "inwardly" or "proximally" and "outwardly" or "distally" refer to directions toward and away from, respectively, the geometric center of the implant and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the implant described herein and the descriptions will focus on the specific features of the individual embodiments that distinguish the particular embodiment from the others As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system, such as, for example, an implant system 10.

The present invention involves a novel technique of atlanto-occipital fixation and fusion. It has the potential to eliminate a staged approach following odontoidectomy. The present invention will allow stabilization to be performed from the initial endonasal approach. This will eliminate the second stage from a posterior approach. The present invention has the potential to reduce operating room time, blood loss and post-operative pain resulting. In addition, it could reduce healthcare costs for this kind of procedure.

Preferred embodiments of the present application are directed to an implant system 10. It should be understood that while the various embodiments of the implant system 10 will be described in connection with atlanto-occipital fixation and fusion surgery, those skilled in the art will appreciate that the implant system 10, as well as the components thereof, may be used for implantation into other parts of the body, including, for example, C1/2 lateral mass joints through the same approach.

The various embodiments of the implant system 10 are preferably sized and configured to be implanted between the occipital condyle and the C1 lateral mass. The implant system 10 may be adapted for use in the posterior approach for atlanto-occipital fusion.

The implant system 10 of each of the embodiments includes a body 20 having a spacer section 30 and a plate section 40. The spacer section 30 is preferably sized and configured for implantation into the joint between the occipital condyle and the C1 lateral mass. The spacer section 30 of each of the embodiments includes an occipital condyle engaging surface 50 located at the top of the spacer section 30, and a C1 lateral mass engaging surface 60 located at the bottom of the spacer section 30. The occipital condyle engaging surface 50 and the C1 lateral mass engaging surface 60 are suitable for contacting and are adapted for being secured relative to the end plates of the occipitocervical ("OC") joint. The spacer section 30 is preferably sized and configured to fix the position of the occipital condyle to the C1 lateral mass and allow for fusion of the joint via a graft. Accordingly, the occipital condyle engaging surface 50 and the C1 lateral mass engaging surface 60 may include a series of teeth, ridges, spikes or other similar projections 180 to aid in securing the implant system 10 to the endplates of the OC joint. In some embodiments, the body 20 is from about 8 to about 12 mm wide and from about 15 to about 20 mm long.

In some of the embodiments, the occipital condyle engaging surface 50 is disposed relative to the C1 lateral mass engaging surface 60 at a selected angular orientation 100. In some of the embodiments, the selected angular orientation 100 is from about 10 degrees to about 20 degrees. In other embodiments, the selected angular orientation 100 is about 15 degrees.

The occipital condyle engaging surface 50 and the C1 lateral mass engaging surface 60 may also include a curved or a tapered surface to help provide an anatomical shape for mating with the patient's articular morphology. The particular surface shape and curvature, taper or alternate surface feature in the anterior-posterior direction, as well as the particular surface shape and curvature, taper or alternate surface feature in the medial-lateral direction will depend upon the location where the implant system 10 is intended to be implanted and/or surgeon preferences or whether the implant system 10 is utilized in another area in the body.

The spacer section 30 may also include one or more boreholes, openings, windows or channels for receiving bone graft material. For example, the body 20 may include one or more vertical openings, windows or channels extending through the spacer section 30 from the occipital condyle engaging surface 50 to the C1 lateral mass engaging surface 60 for insertion of bone graft material, such that bone growth is promoted through the vertical openings, windows or channels following implantation of the implant system 10. In one embodiment, a single graft hole 90 is located in the spacer section 30. In some embodiments, the graft hole 90 is from about 3 to about 5 mm wide and about 8 to about 12 mm long. In some embodiments, the graft hole 90 incorporates bone material including autograft, allograft, iliac crest bone, rib bone, xenograft or transgenic cortical and/or corticocancellous bone. In some embodiments, the implant system 10 retains the bone graft material in proper position and under compression to facilitate fusion between the occiput and the C1 lateral mass.

The plate section 40 provides anchoring points for the implant via openings 70, 80 for the bone fixation fasteners 130, 140. In some embodiments, the plate section 40 optimally orients the trajectory of bone fixation fasteners 130, 140 during implantation. The plate section 40 also serves to increase implant stability.

Figure 2:
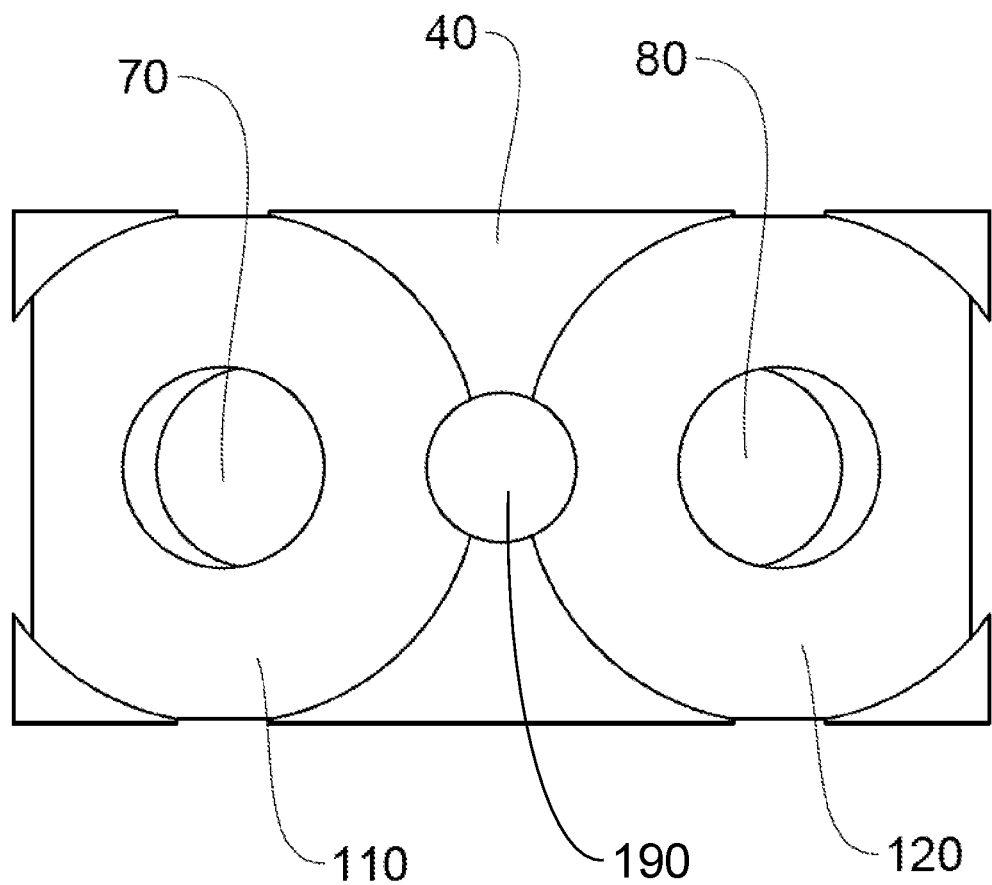
FIG. 2 illustrates an anterior view of an implant according to an embodiment of the present application.
Figure 3:
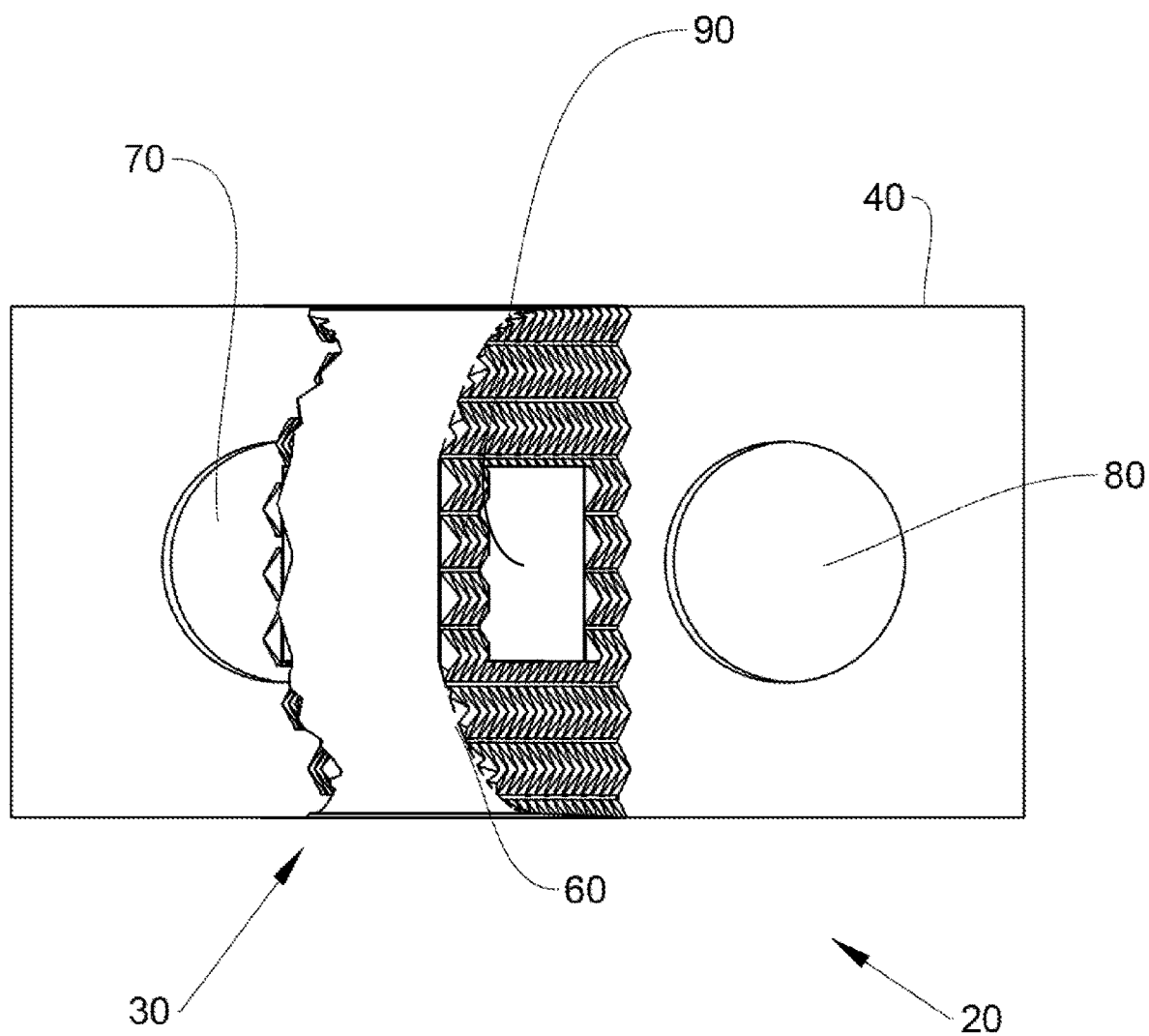
FIG. 3 illustrates a posterior view of an implant according to an embodiment of the present application.
Figure 4:
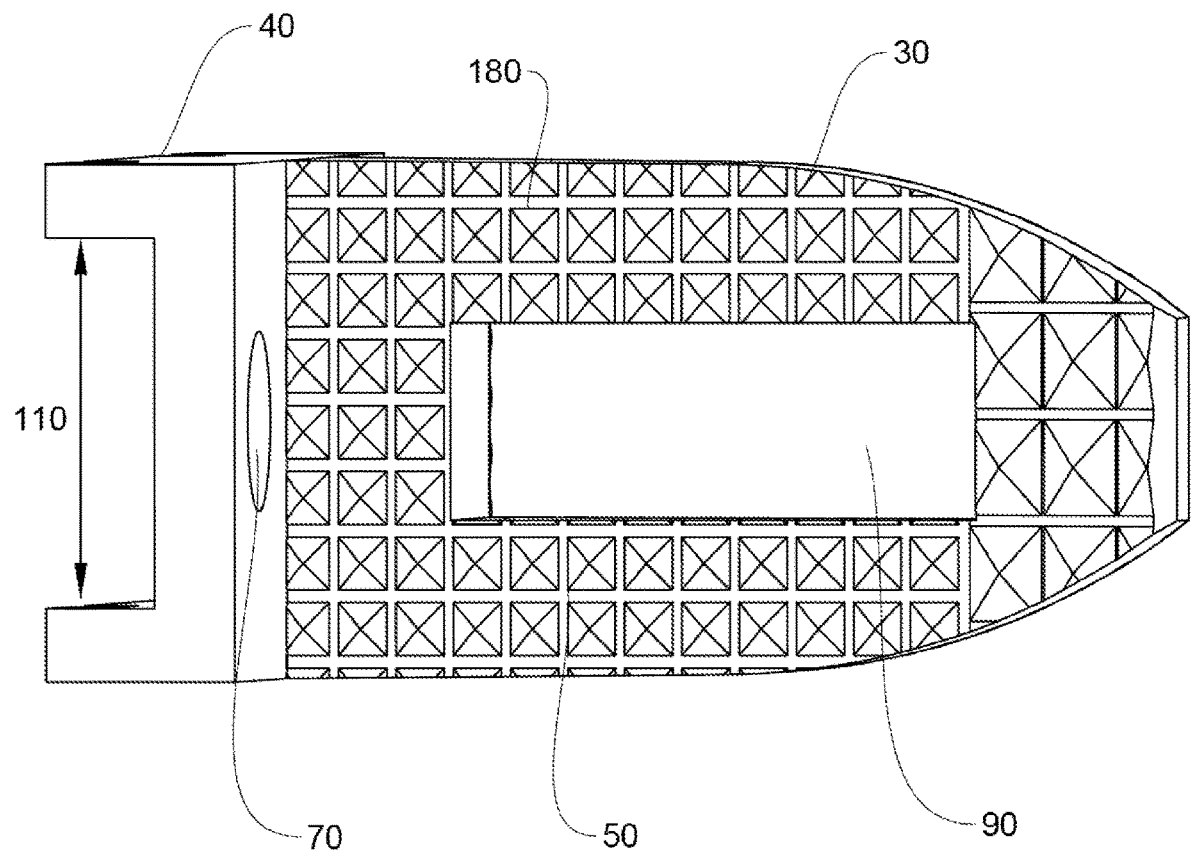
FIG. 4 illustrates a top view of an implant according to an embodiment of the present application.
Figure 5:
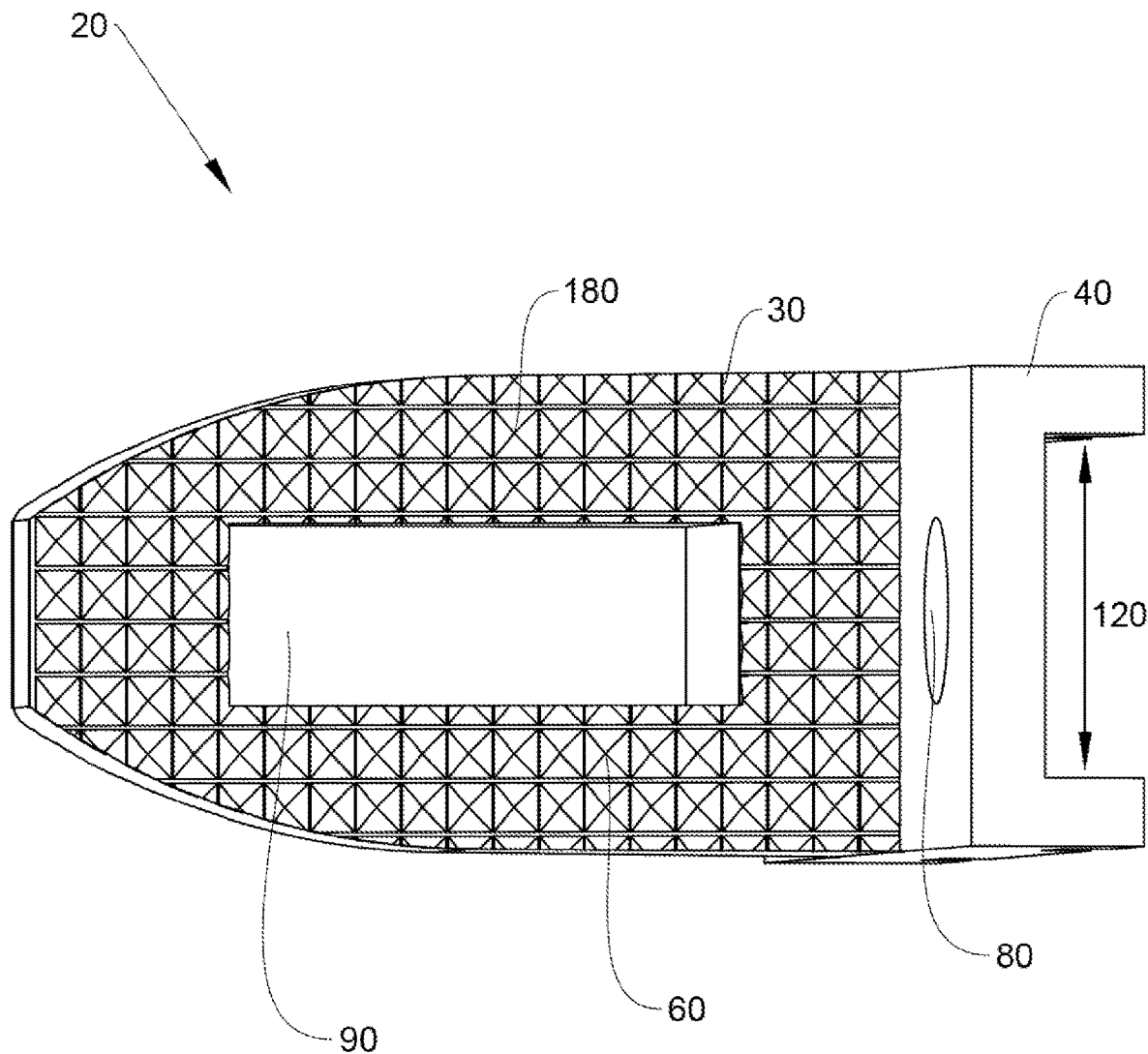
FIG. 5 illustrates a bottom view of an implant according to an embodiment of the present application.
Figure 6:
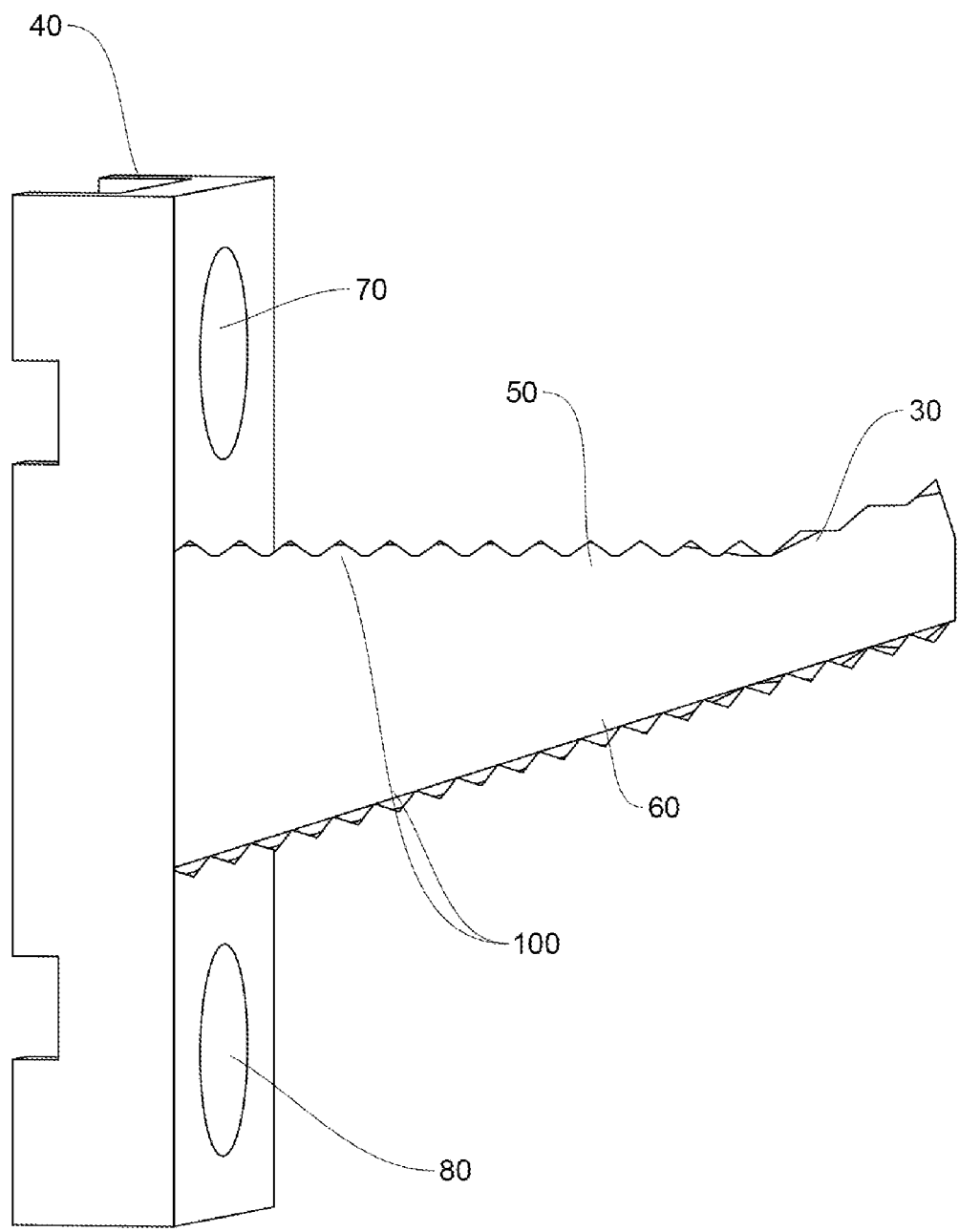
FIG. 6 illustrates a right side view of an implant according to an embodiment of the present application.
Figure 7:
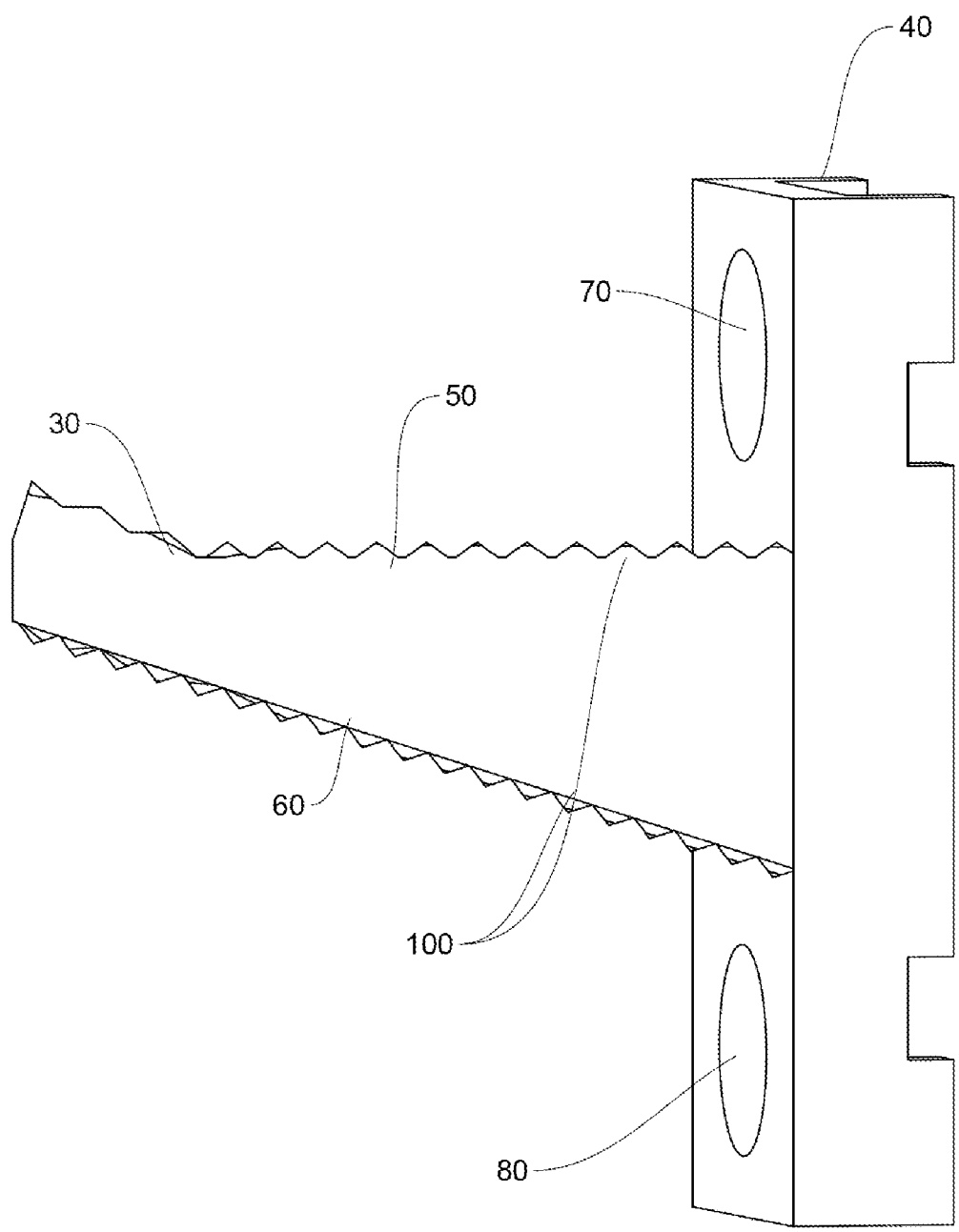
FIG. 7 illustrates a left side view of an implant according to an embodiment of the present application.
Figure 8A:
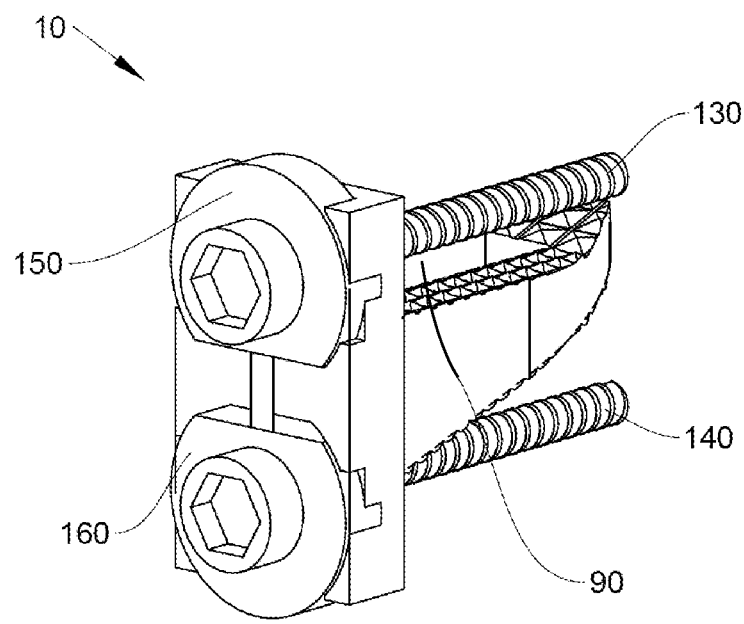
FIG. 8A is an image showing a perspective view of an implant system according to an embodiment of the present invention.
Figure 8B:
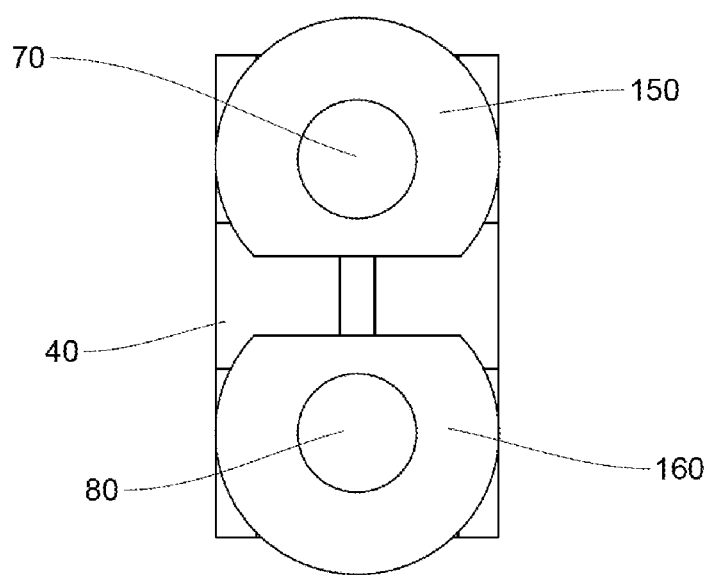
FIG. 8B is an image showing an anterior view of an implant system according to an embodiment of the present invention.
Figure 8C:
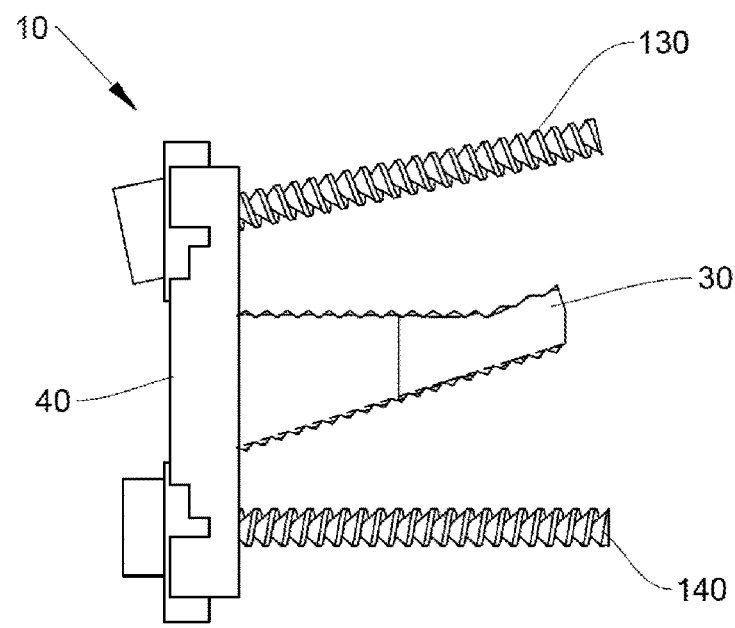
FIG. 8C is an image showing a right side view of an implant system according to an embodiment of the present invention.
Figure 8D:
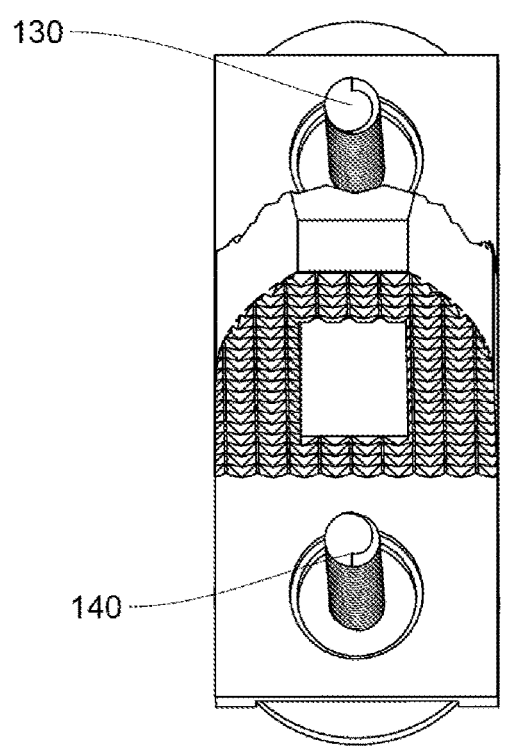
FIG. 8D is an image showing a posterior view of an implant system according to an embodiment of the present invention.

The plate section 40 preferably includes a tool engagement feature (not shown) for engaging one or more insertion tools. The tool engagement feature may be in any form now or hereafter known for such purpose including one or more recesses (not shown) formed in the anterior surface of the plate section 40, for engaging arms of the insertion tool (not shown). Alternatively, the tool engagement feature may be a threaded bore (not shown) formed in the anterior surface of the plate section 40 for engaging a threaded stem extending from the insertion tool, etc. FIG. 2 also shows a central hole 190 that can be used to secure a device, for example the tip of a screwdriver, which can be used to insert the implant system 10.

The plate section 40 preferably includes at least two openings 70, 80 for receiving at least two bone fixation fasteners 130, 140, preferably bone screws so that, in use, after the implant body 20 has been inserted into the prepared space between the occipital condyle and the C1 lateral mass, the body 20 may be secured to the occipital condyle and the C1 lateral mass. The bone fixation fasteners 130, 140 preferably include a threaded shaft and a partially spherical head portion that is generally smooth where it contacts the opening 70 or 80. The threaded shaft may be self-drilling, i.e. does not necessitate the drilling of pilot holes, but are not so limited. The bone fixation fasteners 130, 140 are not limited to bone screws and may be comprised of a helical nail, a distally expanding nail or screw, etc. The openings 70, 80 are preferably sized and configured so that the head portion of the bone fixation fasteners 130, 140 do not protrude proximally beyond the anterior surface of the plate section 40, when the bone fixation fasteners 130, 140 have been fully implanted.

In some embodiments, the plate section 40 includes a first washer cavity 110 and a second washer cavity 120. In these embodiments, the first opening 70 is located in the center of the first washer cavity 110, and the second opening 80 is located in the center of the second washer cavity 120. A first washer 150 is placed in the first washer cavity 110 and a second washer 160 is placed in the first washer cavity 120. The washers 150, 160 strengthen the connection between the plate section 40 and the bone fixation fasteners 130, 140. In some embodiments, the washers 150, 160 are placed in the washer cavities 110, 120 prior to insertion of the implant body 20.

The plate section 40 preferably includes at least first and second openings 70, 80 for receiving at least first and second bone fixation fasteners 130, 140. In some embodiments, the first bone fixation fastener 130 is not angled. In other words, it is in a "neutral" (i.e. horizontal) position. In other embodiments, the first bone fixation fastener 130 is angled upwardly for engaging the occipital condyle. In some embodiments, the second bone fixation fastener 140 is not angled. In other embodiments, the second bone fixation fastener 140 is angled downwardly for engaging the C1 lateral mass. That is, in some embodiments at least the first or second opening 70, 80 has a longitudinal axis that is oriented obliquely with respect to the plate section 40 so that the bone fixation fasteners 130, 140 form a fastener angle with respect to the occipital condyle engaging surface 50 of the spacer section 30 or the C1 lateral mass engaging surface 60 of the spacer section 30 wherein bone fixation angle may be in the range between zero degrees (0°) and forty five degrees (45°), and more preferably between fifteen degrees (15°) and thirty degrees (30°). The bone fixation angle may be the same for all of the openings 70, 80 or may be different for each of the openings 70, 80. As would be understood by one of ordinary skill in the art based upon a reading of this disclosure, a plurality of potential angles is possible.

It should be understood however that the implant system 10 may include any number of openings 70, 80 configured to receive a corresponding number of bone fixation fasteners 130, 140 in any number of configurations. In addition, the number of bone fixation fasteners 130, 140 extending from the plate section 40 may be varied and the number of bone fixation fasteners 130, 140 extending into the occipital condyle need not equal the number of bone fixation fasteners 130, 140 extending into the C1 lateral mass.

The implant system 10 preferably includes a retention mechanism for reducing the likelihood that the bone fixation fasteners 130, 140 may postoperatively uncouple from the plate section 40 and migrate from the OC joint. In use, the retention mechanism preferably engages or contacts the bone fixation fasteners 130, 140 or blocks or covers at least a portion of the bone fixation holes 40 and hence the bone fixation fasteners 130, 140 to prevent the bone fixation fasteners 130, 140 from backing-out.

The implant system 10 including the body 20, the bone fixation fasteners 130, 140 and the washers 150, 160 may be fabricated from biologically acceptable materials suitable for medical applications, including metals, synthetic polymers, ceramics and bone material and/or their composites. For example, the components of implant system 10, individually or collectively, can be fabricated from materials such as carbon fiber, stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corralline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof. In one embodiment, the body 20 is made from NylonX, which incorporates 80% nylon and 20% carbon fiber. In some embodiments, the material used for the body 20 is 3D printed. In another embodiment, the material used for the body 20 is printed on the Prusa i3, which allows personalization of the internal patterns of the implant.

Various components of the implant system 10 may have material composites, including the above materials, to achieve various desired characteristics such as strength, rigidity, elasticity, compliance, biomechanical performance, durability and radiolucency or imaging preference. The components of the implant system 10, individually or collectively, may also be fabricated from a heterogeneous material such as a combination of two or more of the above-described materials. The components of the implant system 10 may be monolithically formed, integrally connected or include fastening elements and/or instruments, as described herein.

As will be appreciated by one of ordinary skill in the art, the implant system 10, or portions thereof, may also be coated with various compounds to increase bony on-growth or bony in-growth, to promote healing or to allow for revision of the implant system 10, including hydroxyapatite, titanium-nickel, vapor plasma spray deposition of titanium, or plasma treatment to make the surface hydrophilic.

Referring to FIGS. 1-9, the implant system 10 of a first embodiment includes a body 20 having a spacer section 30 and a plate section 40. The spacer section 30 of each of the embodiments includes an occipital condyle engaging surface 50 located at the top of the spacer section 30, and a C1 lateral mass engaging surface 60 located at the bottom of the spacer section 30. The plate section 40 preferably includes at least two openings 70, 80 for receiving at least two bone fixation fasteners 130, 140. The spacer section 30 also includes a graft hole 90. The occipital condyle engaging surface 50 is disposed relative to the C1 lateral mass engaging surface 60 at a selected angular orientation 100. The occipital condyle engaging surface 50 and the C1 lateral mass engaging surface 60 may include a series of teeth, ridges, spikes or other similar projections 180 to aid in securing the implant system 10 to the endplates of the OC joint. In one embodiment, the projections 180 are a hexagonal infill pattern with 90% density.

Referring to FIGS. 2, 8A, 8B, 8C and 8D, the plate section 40 of an embodiment includes a first washer cavity 110 and a second washer cavity 120. In these embodiments, the first opening 70 is located in the center of the first washer cavity 110, and the second opening 80 is located in the center of the second washer cavity 120. A first washer 150 is placed in the first washer cavity 110 and a second washer 160 is placed in the first washer cavity 120. The bone fixation fasteners 130, 140 are inserted through the washers 150, 160 and openings 70, 80, Attachment of the implant system 10 to the occiput is completed by the attachment of the plate section 40 to the occipital condyle with at least a first bone fixation fastener 130 passing through first washer 150 and first opening 70. Attachment of the implant system 10 to the atlas is completed by the attachment of the plate section 40 to the C1 lateral mass with at least a second bone fixation fastener 140 passing through second washer 160 and second opening 80. In some embodiments, multiple additional bone fixation fasteners may be used in different openings. Where appropriate, paths for the insertion of the bone fixation fasteners 130, 140 may be drilled prior to insertion.

Figure 10:
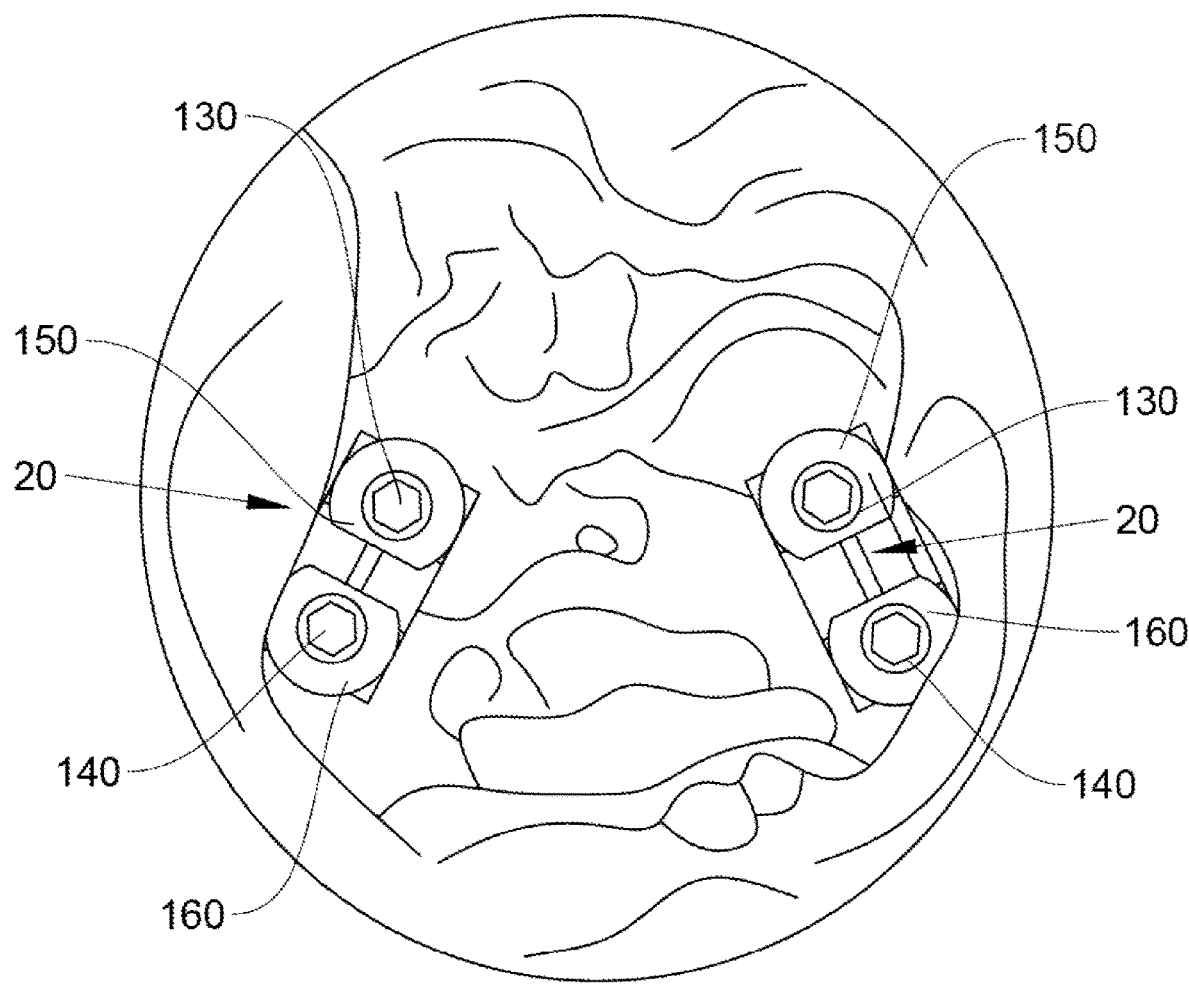
FIG. 10 is an image of a successful insertion via an endoscopic endonasal approach of two implant systems according to an embodiment of the present invention in a cadaver.

FIG. 10 is an image of a successful insertion via an endoscopic endonasal approach of two implant systems according to an embodiment of the present invention in a cadaver. The bone fixation fasteners 130, 140 are inserted through the washers 150, 160 and embedded in the bone, securing the body 20.

Figure 11A:
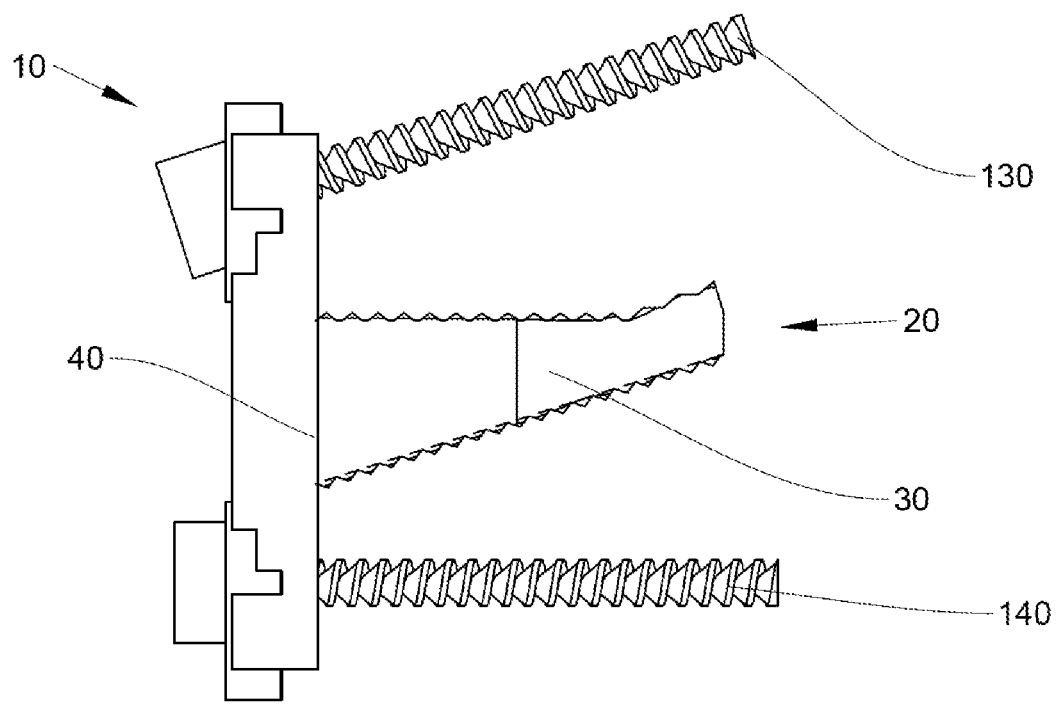
FIG. 11A is an image showing a right side view of an implant system according to another embodiment of the present invention.
Figure 11B:
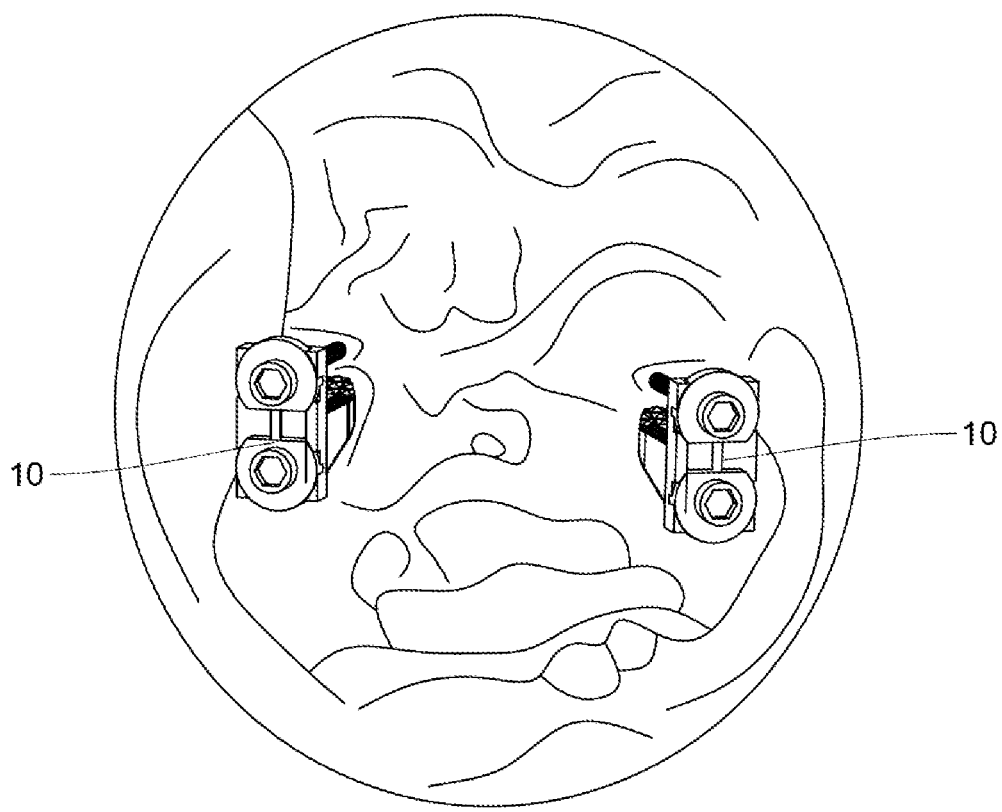
FIG. 11B is an image of a successful insertion via an endoscopic endonasal approach of two implant systems similar to the one shown in FIG. 11A in a cadaver.

FIG. 11A shows an alternative embodiment of an implant system 10. The body 20 has a spacer section 30 and a plate section 40. The plate section 40 has bone fixation fasteners 130, 140 inserted through it. FIG. 11B is an image of a successful insertion via an endoscopic endonasal approach of two implant systems similar to the implant system 10 of FIG. 11A in a cadaver.

Figure 12A:
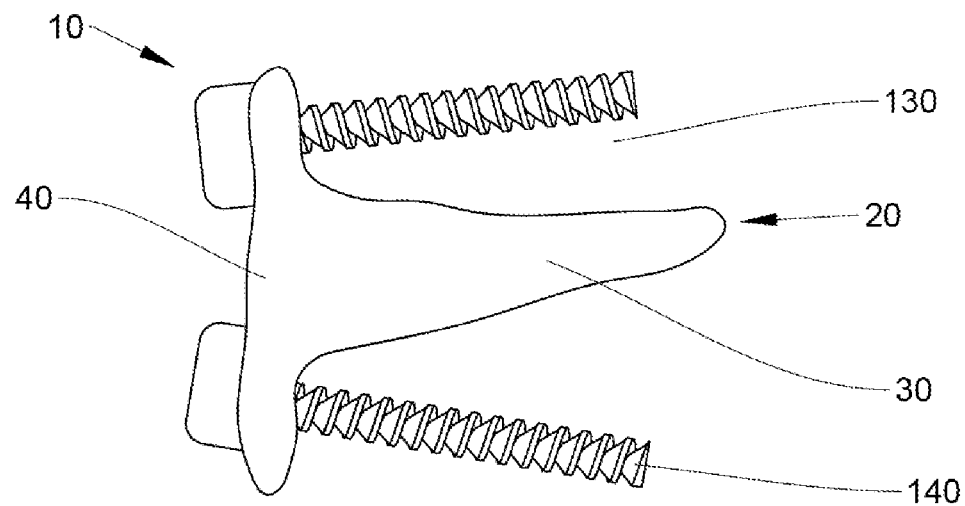
FIG. 12A is an image showing a right side view of an implant system according to another embodiment of the present invention.
Figure 12B:
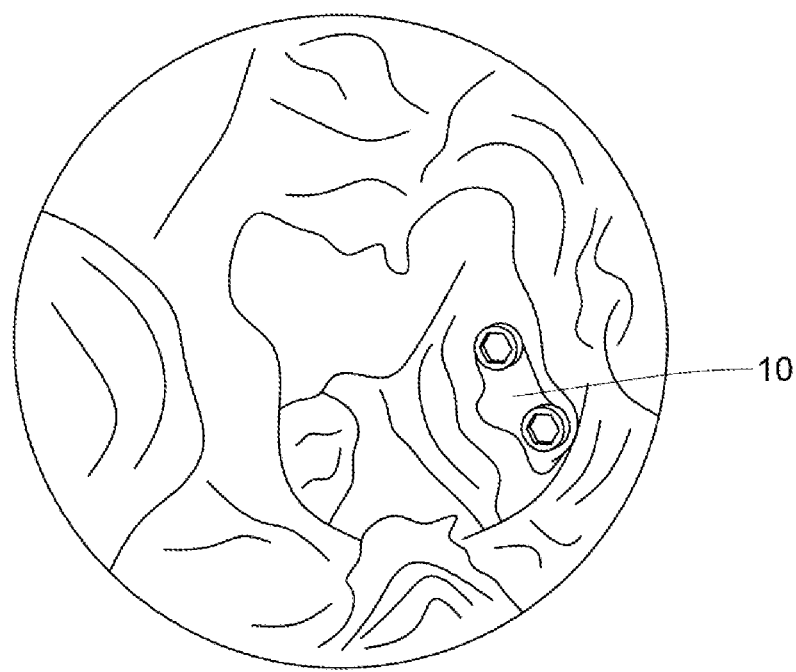
FIG. 12B is an image of a successful insertion via an endoscopic endonasal approach of an implant system similar to the one shown in FIG. 12A in a cadaver.

FIG. 12A shows an alternative embodiment of an implant system 10. The body 20 has a spacer section 30 and a plate section 40. The plate section 40 has bone fixation fasteners 130, 140 inserted through it. FIG. 12B is an image of a successful insertion via an endoscopic endonasal approach of one implant system similar to the implant system 10 of FIG. 12A in a cadaver.

Figure 13A:
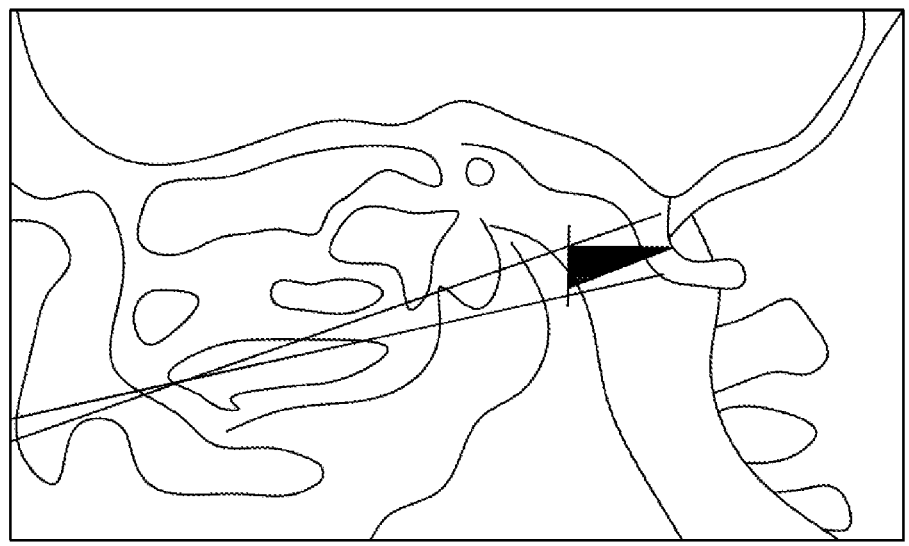
FIG. 13A is an illustration showing an implant and screw trajectory in the sagittal plane according to an embodiment of the present invention.
Figure 13B:
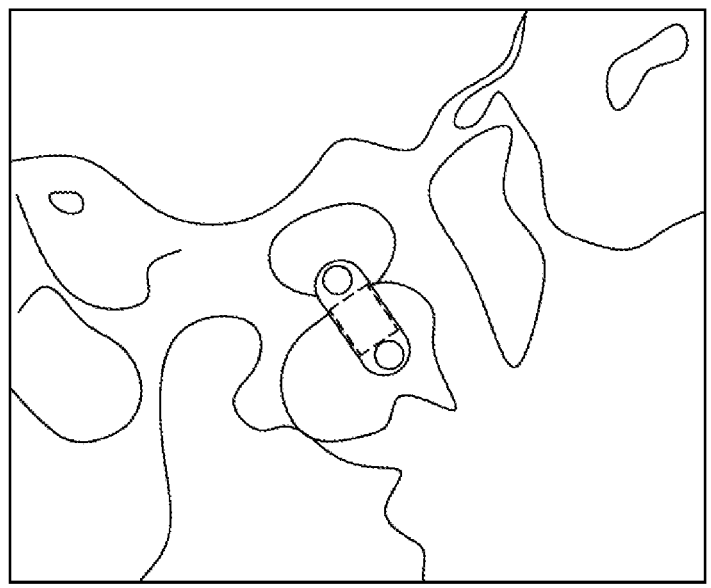
FIG. 13B is an illustration showing an implant and screw trajectory in the coronal plane according to an embodiment of the present invention.

FIG. 13A shows an implant and screw trajectory in the sagittal plane according to an embodiment of the present invention. FIG. 13B shows an implant and screw trajectory in the coronal plane according to an embodiment of the present invention. The orientation in the coronal plane is dictated by the angle of the joint as the implant is inserted parallel to this angle.

It will be appreciated that systems and methods of the present invention may be used to treat craniocervical junction instability through fusion of the occiput-C1 region, where the instability results from any cause, so long as the patient is sufficiently healthy to undergo implantation surgery and the patient's anatomy will allow successful implantation. Examples of causes of such instability that may be treated with the systems and methods of the present invention include trauma, rheumatoid arthritis pannus formation, basilar invagination. Chiari 1 malformation, os odontoideum, congenital anomaly (such as Down syndrome, Stihl disease, metatrophic dwarf, Morquio syndrome, Klippel-Feil syndrome, axis assimilation, or skeletal dysplasia), neoplasm, or chronic instability.

Method

The present invention uses an endoscopic endonasal surgical technique to reach the skull base and top of the spine directly by operating through the nose and sinuses. An endoscope provides light and a lens for viewing and transmitting internal images. Specialized instruments are used alongside the endoscope to perform the procedure. For example, a high speed drill with a diamond ball bit can be used to remove bone material, a hexagonal screw driver can be used to insert an implant and the same screw driver can be used to secure bone screws. This screw driver is the same diameter as the central hole of the plate of the implant and fits securely utilizing friction to keep plate attached.

The present invention particularly concerns an endoscopic endonasal approach to achieve atlanto-occipital fixation and fusion. Conditions in which the odontoid ventrally compresses the brainstem or spinal cord often present as lower cranial neuropathies, sensorimotor deficits and/or myelopathy necessitating decompression and subsequent stabilization and fusion. Following endonasal odontoidectomy, it is common for patients to require arthrodesis across O-C1 and C1-2. The present invention uses a novel implant to achieve arthrodesis of the 0-C1 joint without requiring a posterior surgery.

Initial methodology for the present invention consisted of the design and 3-D printing of an implant followed by its successful implantation in a cadaver specimen. A CT scan of a cadaver specimen was obtained and utilized in the modeling of the occipito-cervical ("OC") joint. An interarticular implant with incorporated anterior plate according to the present invention was designed and printed using Polylactic acid for prototyping. Refinement of the implant design and implant insertion technique was done prior to printing using carbon fiber material. Screw trajectory and placement was studied and determined based on a CT scan of the specimen.

In one embodiment, the procedure for implantation consists of endoscopic endonasal exposure of the OC joint bilaterally using previously described techniques. The trajectory of implant insertion is parallel to the posterior aspect of saddle shape of the OC joint. The anterior superior aspect of C1 lateral mass is drilled away using a high speed drill with a 3 mm matchstick bit to a height and width equal to that of the implant. This exposes the posterior aspect of the joint which is in-line with the trajectory of the present approach as well as exposing cancellous bone required for fusion. Additionally, the occipital condyle is decorticated, exposing cancellous bone necessary to stimulate boney fusion. This bony work allows for the implant to be supported by the cortex of the C1 lateral mass joint articulating surface posteriorly and a rim of cortex of the anterior wall of C1 lateral mass anteriorly. The articulating surface of the occipital condyle rests on the superior surface of the implant. A nutrient hole in the implant houses autograft from odontoidectomy or allograft. The incorporated plate abuts the occipital condyle and C1 lateral mass anterior wall and a screw is placed through each hole providing rigid fixation.

EXAMPLES

Design of Construct

A combination of cadaveric dissections, radiographic imaging, anatomical texts, and publications was used to develop a preliminary design of an intraarticular-screw construct amenable to endonasal delivery. The implant was designed to occupy the interspace between the inferior surface of the occipital condyle and the superior surface of the C1 lateral mass. Fixation to the occipital condyle and C1 lateral mass was obtained using delivery of modular titanium screws that directly transgressed the face of the implant.

Prior to instrumentation, all heads were scanned using a high-resolution (64-slice), fine-cut CT scanner and registered to neuronavigation.

Example 1

Figure 9:
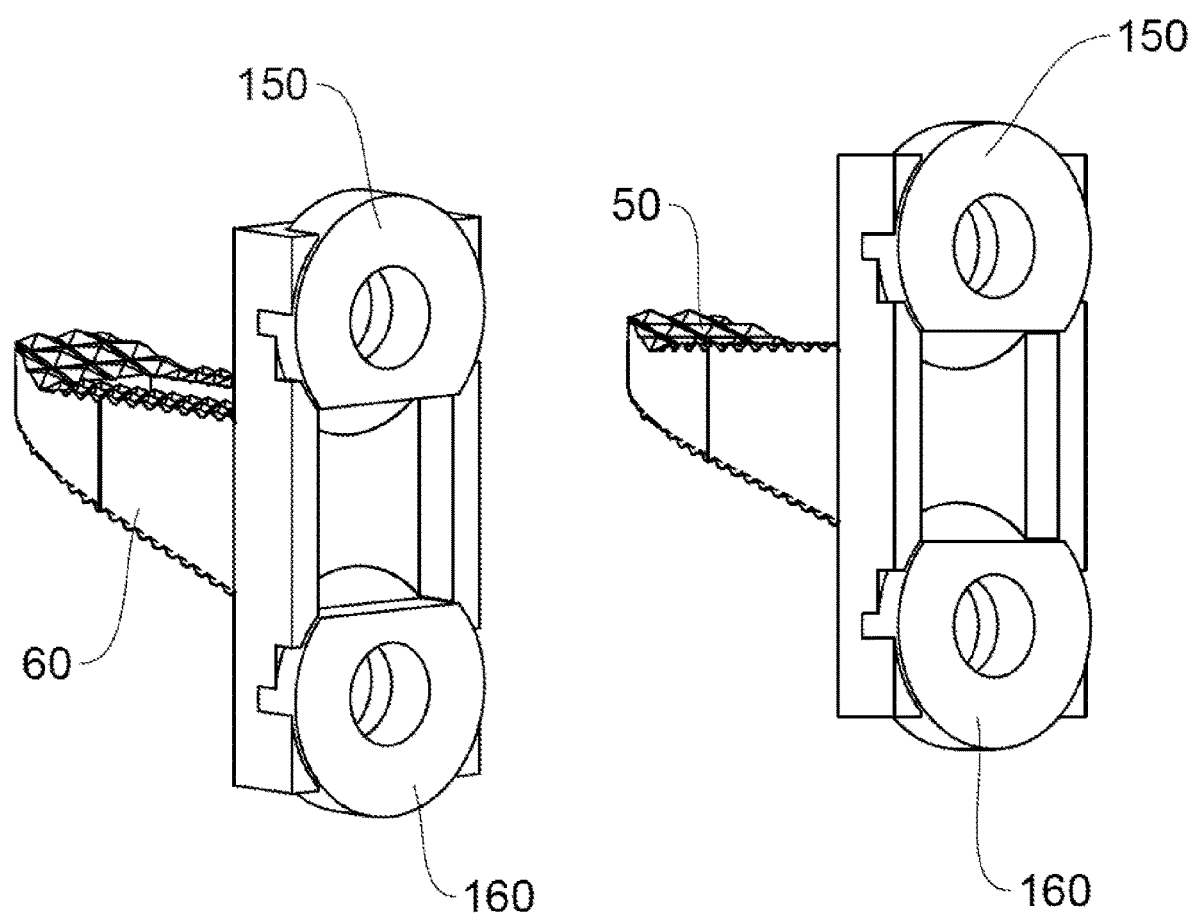
FIG. 9 is an image showing an anterior perspective view of two implant systems according to an embodiment of the present invention.

The nasopharynx of a head specimen was approached using a binostril approach with removal of the inferior portion of the posterior septum. A 30 cm, zero-degree endoscope was utilized for visualization. An inverted "U-Shaped" myomucosal flap incision was used to create a flap which could be retracted for exposure of the O-C1 junction and C1-2 junction. The O-C1 joint was decorticated bilaterally using a 3 mm cutting ball bit. An implant system as shown in FIGS. 8 and 9 was inserted into each of the two joints until plate tight against the anterior aspect of the occipital condyl and the lateral mass of C1. A drill was used to create a pilot hole in the bone through an opening in the plate section of the implant. 22 mm screws were inserted through the plate openings using navigation to determine ideal trajectory.

Radiographic Analysis

A CT head scan was obtained after the procedure to confirm proper placement of implants and screws.

Biomechanical Assessment

The head specimen of Example 1 had pipe inserted from forehead to occiput and perpendicular to the chin-brow line. The head was then mounted to a base with a bolt inserted through the pars of C2 horizontally and supported bilaterally by brackets mounted on the base. Additionally, a pointed bolt was inserted through posterior ring of C1 and secured to a bracket also mounted on the base. This isolated motion of the head exclusively to the OC joint. Long, thin, marker rods were inserted into the C1 lateral mass and skull base in the sagittal plane. The marker rods were used to measure angular displacement. A 2 Nm moment was applied to the pipe anteriorly using a mechanical testing system. A picture was taken from lateral position and a protractor app was used to measure the angle to be 10.6 degrees. This was then repeated applying the 2 Nm moment to the pipe posteriorly. A picture was taken from lateral position and a protractor app was used to measure the angle to be −16.3 degrees. Our total baseline angular range of motion was calculated to be 26.9 degrees. The cadaver specimen was removed from the mount and the pipe was removed from the head for preparation of the procedure. After the procedure, the pipe was reinserted and the head remounted as described above. Flexion and extension were tested similarly, and angular range of motion was found to be 3.3 degrees post-procedure. Destructive testing was then performed by applying a progressively increasing force to the pipe anteriorly. The force vs time curve was plotted and the implant appeared to fail at moment of 25.8 Nm All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. An atlanto-occipital fusion method for fixating a 0-C1 joint, comprising:
 a. preparing an endonasal surgical path using a binostril approach comprising:
  i. removing the inferior portion of the posterior septum,
  ii. performing a myomucosal flap incision to create a flap,
  iii. retracting the flap to expose the O-C1 joint,
 b. bilaterally decorticating the O-C1 joint,
 c. drilling a nutrient hole in the occipital condyle, and
 d. inserting an implant into each side of the decorticated 0-C1 joint;
 wherein the implant comprises:
  a body having a spacer section and a plate section;
   i. the spacer section comprising an occipital condyle engaging surface and a C1 lateral mass engaging surface, the occipital condyle engaging surface being disposed relative to the C1 lateral mass engaging surface at a selected angular orientation;
   ii. the plate section defining at least a first opening and a second opening; and
  at least two bone fixation fasteners; a first fastener disposed with the first opening, and a second fastener disposed with the second opening; wherein
  the first fastener being engageable with the plate and capable of fixing with the occipital condyle and the second fastener being engageable with the plate and capable of fixing with the C1 lateral mass.

2. The method of claim 1 wherein the inserted implant is supported by the cortex of the C1 lateral mass joint articulating surface posteriorly and a rim of cortex of the anterior wall of C1 lateral mass anteriorly.

3. The method of claim 1 wherein the inserted implant further comprises at least a first washer and a second washer, the first washer being disposed with the first opening and the second washer being disposed with the second opening.

4. The method of claim 1 wherein the selected angular orientation of the occipital condyle engaging surface relative to the C1 lateral mass engaging surface is from about 10 degrees to about 20 degrees.

5. The method of claim 4 wherein the selected angular orientation is about 15 degrees.

6. The method of claim 1 wherein the first opening and the second opening are threaded bore holes.

7. The method of claim 6 wherein the threaded bore holes of the first and second openings direct the first and second fasteners at the same angular orientation.

8. The method of claim 6 wherein the threaded bore holes of the first and second openings direct the first and second fasteners at different angular orientations.

9. The method of claim 1 wherein the occipital condyle engaging surface and the C1 lateral mass engaging surface comprise projections selected from the group consisting of teeth, ridges, spikes and combinations thereof.

10. The method of claim 9 wherein the spacer section has one graft hole that is from about 3 to about 5 mm wide and about 8 to about 12 mm long.

11. The method of claim 10 wherein the graft hole contains autograft, allograft or a combination thereof.

12. The method of claim 1 wherein the spacer section has one or more graft holes.

13. The method of claim 1 wherein the inserted implant comprises two or more bodies having the same configuration.

14. The method of claim 1 wherein the body of the inserted implant comprises a material selected from the group consisting of carbon fiber, polylactic acid, stainless steel alloys, commercially pure titanium, titanium alloys, ceramics, thermoplastics, polyethylene terephthalate (PET), fabric, silicone, polyurethane, silicone-polyurethane copolymers, polymeric rubbers, polyolefin rubbers, hydrogels, semi-rigid and rigid materials.

15. The method of claim 1 wherein the body of the inserted implant comprises carbon fiber.

16. The method of claim 1 wherein the bone fixation fasteners are selected from the group consisting of bone screws, helical nails, distally expanding nails, and distally expanding screws.

* * * * *